United States Patent [19]
Kite

[11] Patent Number: 5,221,262
[45] Date of Patent: Jun. 22, 1993

[54] HYPODERMIC NEEDLE RETRACTOR

[75] Inventor: John P. Kite, Dubbo, Australia

[73] Assignee: Teskit Corporation Pty. Ltd., Victoria, Australia

[21] Appl. No.: 585,089

[22] PCT Filed: Mar. 21, 1989

[86] PCT No.: PCT/AU89/00121
§ 371 Date: Sep. 20, 1990
§ 102(e) Date: Sep. 20, 1990

[87] PCT Pub. No.: WO89/09075
PCT Pub. Date: Oct. 5, 1989

[51] Int. Cl.⁵ .............................................. A61M 5/00
[52] U.S. Cl. ..................................... 604/110; 604/195
[58] Field of Search ............... 604/195, 187, 110, 218, 604/198; 128/763, 764, 765

[56] References Cited
U.S. PATENT DOCUMENTS
4,692,156 9/1987 Haller ................................... 604/195

FOREIGN PATENT DOCUMENTS
8900435 7/1987 World Int. Prop. O. .......... 604/110

Primary Examiner—John D. Yasko
Attorney, Agent, or Firm—Gifford, Groh, Sprinkle, Patmore and Anderson

[57] ABSTRACT

A hypodermic syringe (10) has a retractable needle (18) carried in A hypodermic syringe (10) has a retractable needsyringe body (11). The needle (18) is attached to a needle holder (22) which has a conical head (26) on its forward end. A passage (30) in the holder enables the needle bore to communicate through holes (29) in the holder (22) with the chamber (14). The plunger and piston assembly (32) has a piston (33) with a sealing cap (35) engaged therewith. The piston (33) has a forwardly extending tubular portion (39) defining an opening with a tapered wall (40) which engages over the head (26) to lock the head behind an abutment surface (41). At the same time a diaphragm (38) formed by the sealing cap (35) extending across the tubular portion (39) is ruptured so the chamber (14) is no longer sealingly enclosed.

18 Claims, 2 Drawing Sheets

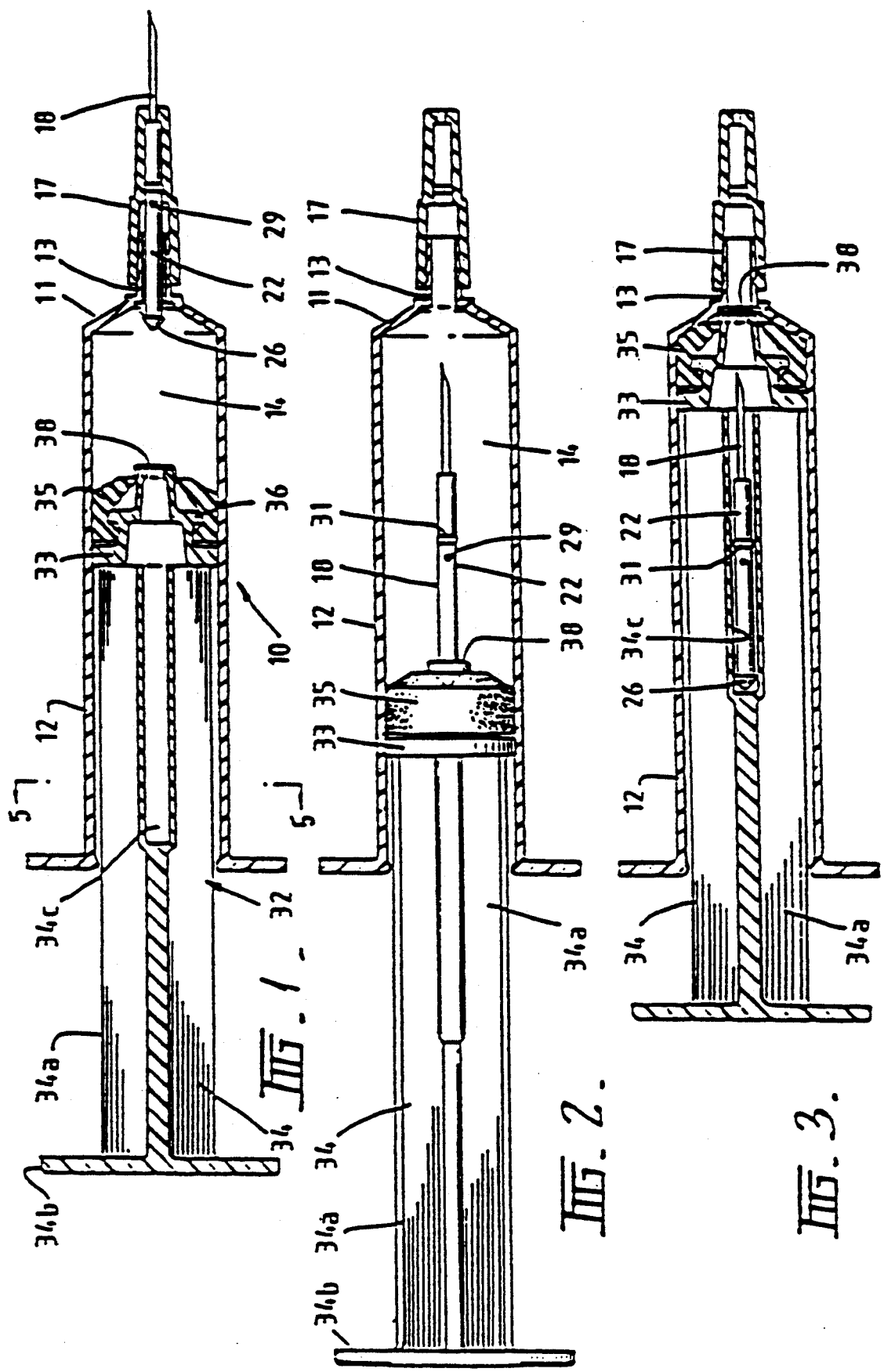

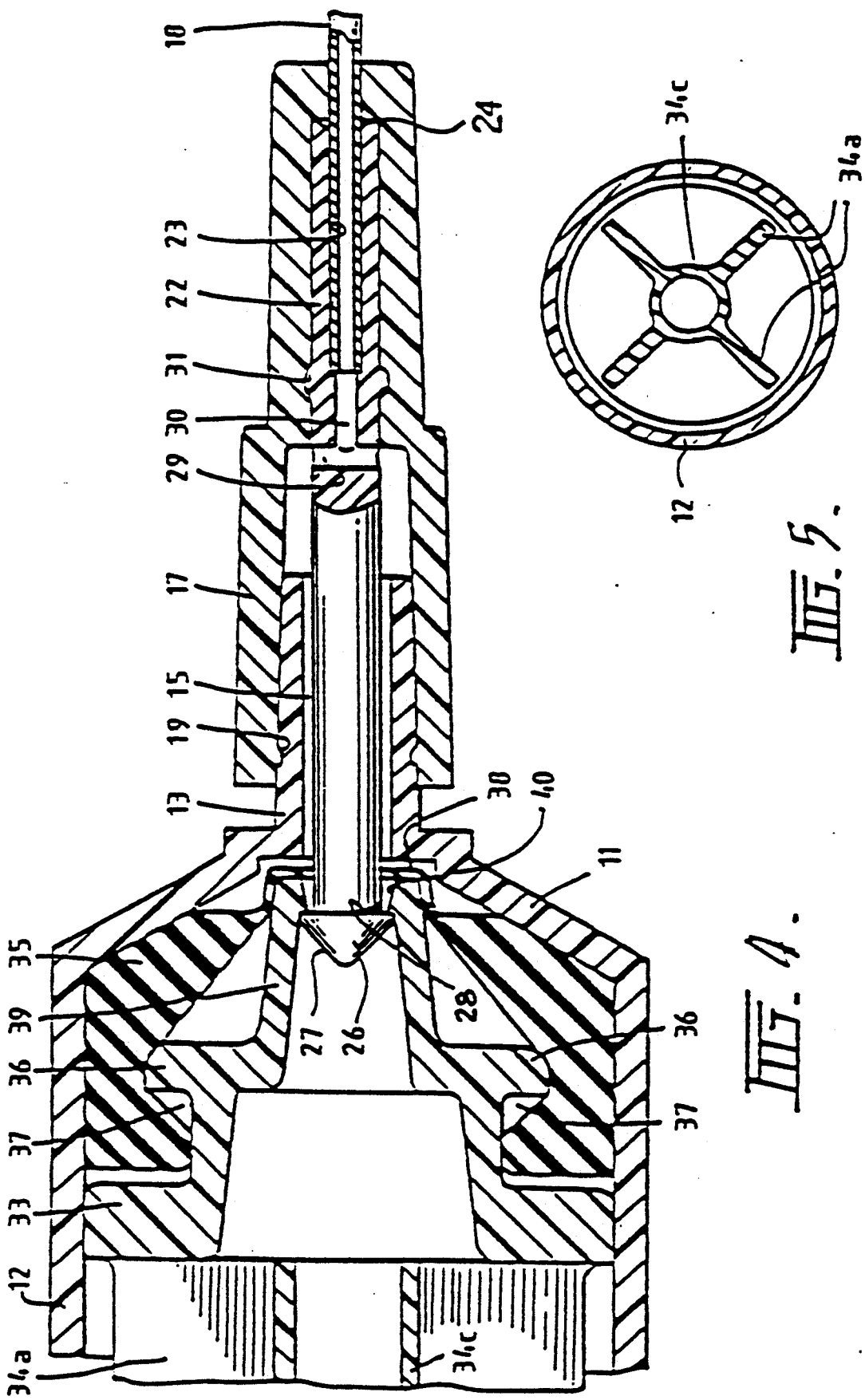

HYPODERMIC NEEDLE RETRACTOR

BACKGROUND OF THE INVENTION

The present invention relates to a syringe and relates particularly to a hypodermic syringe incorporating a needle retractor.

Syringes currently in use have a fixed needle which is kept or sealed with an appropriate shield but which is otherwise permanently fixed to the syringe body for use. After the syringe has been used for the administration of a serum, an antibody or the like, a danger often exists with the exposed needle of the used syringe particularly if the needle has not been safely capped. Also, there is a danger that a used syringe may be reused in which case a danger exists of infection from the now non-sterile syringe.

BACKGROUND ART

Various solutions to the problem of an exposed needle of a syringe, after use, have been proposed. In U.S. Pat. No. 4,026,287 to Haller, it is proposed to form the forward end of the barrel of the syringe as a breakable end wall, the cannula mounted on the end wall being severable therefrom upon retraction of the plunger of the syringe. This, however, can lead to the breakable end wall breaking inadvertently during operation of the syringe or as a result of forces applied to the needle during use.

Various patent specifications have suggested an arrangement whereby the needle of the syringe is mounted in a hub and the syringe plunger can engage with the hub, such as by a screw threaded action, to thereby withdraw the hub from the end of the syringe barrel to retract the needle into the barrel. Such arrangements as are shown in U.S. Pat. Nos. 4,675,005 to DeLuccia, for 4,650,468 to Jennings, 4,710,170 to Haber et al., 4,507,117 to Vining et. al., and 4,592,744 to Walter. The structure of all these syringes is relatively complex, requiring arrangements for engagement of needles within needle holders, engagements of needle holders within syringe barrels so as to seal the needle within the barrel, means for engaging the plunger with the needle holder, generally by a rotational, screw threading or bayonet attachment and relatively complex operation procedures to ensure the disclosed systems are effective.

U.S. Pat. No. 4,770,655 to Haber et. al. discloses a syringe construction in which the piston assembly has a detachable stem and a needle capturing receptacle which is axially and distally movable in the cylinder. When the piston is moved to the most distal aspect of the cylinder it selectively engages the needle. The piston is withdrawn to relocate the needle from the distal end to the proximal cylinder end. The needle capturing receptacle is locked at the proximal end of the cylinder with the needle cannula retracted within and shielded by the cylinder. The stem is detached from the piston assembly and discarded While the arrangement described is relatively simple, and therefore economical to produce, several actions are required in order to render the syringe relatively safe, one of those actions including breaking the stem from the piston assembly. It will be appreciated that un-intended stem breakage can easily occur through mis-use of the syringe, and if the stem is not broken, the syringe can be reused with relatively little difficultly.

SUMMARY OF THE INVENTION

It is desirable to provide an improved construction of hypodermic syringe which is economical to manufacture, has relatively few parts compared to the commonly used, fixed needle syringes, but allows the needle to be retracted and safely stored within the syringe for disposal.

It is another object of the present invention to provide an improved hypodermic syringe which, after use, cannot be reused without replacement parts.

It is another object of the present invention to provide a hypodermic syringe which has a retractable needle and yet which also has a minimal free space.

It is also an object of the present invention to provide a hypodermic syringe having a retractable needle so as to lower the possibility of a used needle entering the skin of a person after the syringe has been used.

Additional objects, advantages and features of the invention will be set forth in the following description or will become apparent by practice of the invention. According to one particular aspect of the invention there is provided a syringe comprising a tubular body open at one end and substantially closed at the other end to provide a chamber, a needle mounting engaged with the said other end, a needle removably mounted in said mounting, the needle having an inner end formed with engageable means, a piston means axially movable within the body, said piston means having gripping means to selectively grip said engageable means when piston means is moved to the closed end of the body whereby subsequent movement of the piston means away from the said closed end draws the needle into the chamber, and a frangible diaphragm on the piston means which is broken with engagement of the engageable means with the gripping means.

In a preferred embodiment of the invention, the needle means includes a needle housing having a substantially axial passageway extending partway along the housing from one end. A hollow needle is secured in the passageway, and at leas one hole in the housing wall communicates with the passageway to allow fluid to pass from the chamber through the needle. The provision of the hole spaced from the inner end of the needle means is an important feature which provides an extremely small minimal volume when the piston is moved to the end of the chamber.

The engageable means on the needle means preferably comprises a substantially conical or tapered head mounted on the needle means so as to provide a radially extending, annular shoulder. The gripping means, in the preferred embodiment, comprises an axially extending, hollow tubular part on the piston, the forward end of which has a tapering surface extending outwardly from a cooperating, annular shoulder. In use, when the piston is moved axially in the chamber towards the needle means, the tapering surface engages with the head of the needle means and snaps over the head so that the cooperating annular shoulder engages behind the head on the needle means.

In one form of the invention, the needle means is carried by a needle support removably attached to the needle mounting. This enables needle assemblies comprising the needle means and support to be replaced on a syringe body. Thus, the body and piston means can be reused with disposable needles. With this arrangement, the needle support and the needle mounting are provided with cooperating means for snap engagement thereof.

In an alternative arrangement, the needle support is fixed to the needle mounting for single use syringes.

In order that the invention will be more readily understood, one embodiment thereof will now be described with reference to the accompanying drawings.

DESCRIPTION OF THE DRAWINGS

FIG. 1 is a cross sectional view of a hypodermic syringe in accordance with the present invention with the needle in the assembled position ready for use, FIG. 2 is a view similar to FIG. 1 but showing the syringe with the needle withdrawn into the chamber, FIG. 3 is a cross sectional elevational view showing the syringe ready for disposal with the needle located within the plunger, FIG. 4 is a detailed view of the needle end of the syringe showing the engagement of the piston with the needle, and FIG. 5 is a cross sectional view taken along the lines V—V of FIG. 1.

DESCRIPTION OF THE PREFERRED EMBODIMENT

The drawings illustrate a hypodermic syringe 10 having a retractable needle 18. In FIG. 1, there is shown the syringe 10 comprising a syringe body 11 having a cylindrical wall 12 extending to an integral needle mounting 13 which substantially closes one end of the body 11. The cylindrical wall 12 defines a generally cylindrical chamber 14 which, in use, contains a liquid to be injected which is expressed from the chamber 14 through a passageway 15 in the needle mounting 13 and through the needle 18.

The syringe 10 is provided with a piston and plunger assembly 32 located in the chamber 14 and axially movable therein. The assembly 32 includes a plunger body 34 formed by four radially extending elongated walls 34A terminating at an outer end in a finger piece 34B. Partway along the plunger body 34, radially inner edges of the walls 34A define a housing 34C.

A piston 33 is integral with the plunger 34 and is provided with a forwardly extending tubular portion 39 which communicates with the housing 34C. The tubular portion 39 terminates in a radially inwardly extending abutment surface 41 from which an outwardly tapering surface 40 extends.

The piston 33 is formed with an annular flange 36 defining an annular groove 37 forming a seat for a seal member 35. The seal member 35 is preferably formed of a soft rubber material and contacts the inner surface of the cylindrical wall 12 of the syringe body 11 to form a liquid seal therewith. The seal member 35 is in the shape of a cap, a central portion of which constitutes a frangible diaphragm or membrane 38 engaged over the end of the tubular portion 39 of the piston 33. The seal member 35 therefore effectively seals the open end of the chamber 14 of the syringe 10 and prevents fluid within the chamber 14 passing into the tubular portion 39 of the piston 33 and into the housing 34C.

The hypodermic needle 18 is fixed within an axial passageway 23 extending from one end of a needle housing 22. The passageway 23 communicates with a further passage 30 and substantially radially extending holes 29 which enable fluid to communicate from the syringe chamber 14 through the hollow needle 18. The needle support 17 is provided with an annular rib 19 which engages a corresponding groove in the needle mounting 13 to snap fit the support 17 in position. Alternatively, the needle support 17 may be fixed, as by gluing or welding, to the needle mounting 13.

Similarly, the needle housing 22 is formed with an annular rib 31 which engages with a corresponding groove in the needle support 17 to hold the hypodermic needle 18 in the operative position. The needle support 17 is formed at its forward end with an annular shoulder 24 which engages the end of the needle housing 22 and prevents forward movement of the hypodermic needle 18 relative to the needle support 17.

The inner end of the needle housing is formed with a conical head 26 defining an annular shoulder 28.

In use of the hypodermic syringe of the invention, the piston and plunger assembly 32 is moved relative to the syringe body 11 to expel liquid within the chamber 14 through the annular space 15 which exist between the needle housing 22 and the needle mounting 13, through the holes 29, the passage 30 and the hollow needle 18. The diaphragm 38 engaged over the end of the piston 33 prevents liquid passing through the tubular portion 39 forming the end of the piston 33.

As the volume of the chamber 14 approaches its minimal volume, the conical surface 27 of the head 24 engages the diaphragm 38 Initially, and subject to the elasticity thereof, the diaphragm 38 deforms around the head 26 until the diaphragm ruptures. Thereafter, the conical surface 27 on the head 26 engages the similarly shaped, cooperating surface 40 on the tubular portion 39, expanding the end of the tubular portion 39 so that the head 26 snaps into the tubular portion 39. In this position, the abutment surface 28 engages the corresponding surface within the tubular portion 39 thus engaging the needle assembly with the piston and plunger assembly 32.

Movement of the piston and plunger assembly 32 axially in the syringe body 11 away from the needle mounting 13 causes the needle housing 22 and attached hypodermic needle 18 to be withdrawn into the chamber 14. Such movement causes the annular rib 31 on the needle housing to disengage from the corresponding groove. In an alternative construction, where no such rib is provided and the needle housing is frictionally held in the needle support 17, the withdrawing forces are sufficient to overcome the frictional holding forces. As the piston and plunger assembly 32 is continually withdrawn to the position illustrated in FIG. 2, the needle 18 is drawn fully into the chamber 14 so as to be located entirely therein. The piston and plunger assembly 32 are then moved forwardly, or the syringe 10 is held vertically with the piston mounting uppermost, so that the needle 18 and needle housing 22 fall into the housing 34C within the plunger body 34. The piston and plunger assembly 32 can then moved to the position shown in FIG. 3 so that the needle and needle housing are captively contained within the housing 34C for safe disposal.

It will be appreciated that any attempt to reuse the syringe will fail due to the ruptured diaphragm 38 preventing pressure being developed within the chamber 14. It will be noted that the housing 34C within the plunger body 34 has openings which communicate with atmosphere Thus, the provision of the frangible diaphragm ensures that the syringe can be used once only without replacement of the seal member.

The structure of the syringe of the present invention is substantially similar to the structure of fixed needle syringes currently in use. Accordingly, the present invention requires minimum re-tooling or modification of existing tooling to be put into practice. Further, it is not necessary for the operator to go through a sequence of operations, such as twisting of the piston and plunger assembly relative to the syringe body, in order to engage the piston with the needle. The simple action of using the syringe automatically engages the piston with the needle and a simple withdrawing of the piston and plunger assembly retracts the needle into the syringe body.

It is envisaged that, subject to cost considerations, automatic retraction of the needle may be provided by mounting a compression spring on the syringe body and biasing the piston and plunger assembly to the outer position. With such a spring biasing arrangement, the operator uses the syringe to inject the fluid and the spring automatically acts to retract the piston and plunger assembly and the attached hypodermic needle into the syringe body without the need for specific operator action.

I claim:

1. A syringe, comprising:
   a tubular body defining a chamber, said tubular body being open at one end to receive a plunger;
   a needle mounting at the other end of said tubular body;
   a needle means removably supported by said needle mounting and projecting from said needle mounting away from said tubular body, said needle means having an inner end within said chamber, said inner end being provided with a head means;
   said piston means connected to said plunger, said piston means being axially movable within said chamber, said piston means including an engaging means at a forward end thereof, said engaging means engaging shoulder means of said needle means located behind said head means when said piston means is moved within said chamber to said other end of said tubular body whereby to grip said needle means so that subsequent movement of said piston means towards said one end draws said needle means into said chamber; and
   a frangible diaphragm means on said piston means, said head means further including a piercing end to rupture said diaphragm means upon engagement of said engaging means with said head means.

2. The syringe according to claim 1 wherein said needle means includes a needle housing having a substantially axial passageway extending partway along said needle housing from one end thereof and a hollow needle secured in said axial passageway, and at least one hole in said needle housing wall communicating with said axial passageway.

3. The syringe according to claim 2 wherein said head means comprises a tapered head on the other end of said needle housing defining a substantially radially outwardly extending, annular shoulder.

4. The syringe according to claim 1 wherein said needle means comprises a hollow needle removably carried in said needle mounting, said needle having an inner end portion formed with an enlarged head, said inner end portion being mounted on said needle.

5. The syringe according to claim 1 wherein said engaging means comprises a tubular extension on said piston means, said tubular extension having a radial abutment surface and a tapered opening which engages over said needle head means.

6. The syringe according to claim 1 wherein said plunger includes a needle receiving housing open at a forward end through said piston to communicate with said engaging means.

7. The syringe according to claim 6 wherein said housing is open to atmosphere external of said chamber.

8. The syringe according to claim 6 wherein said housing comprises a substantially cylindrical wall substantially coaxial with said body, a length greater than the length of said needle means and an inner diameter to freely receive said needle means.

9. The syringe according to claim 1 wherein said frangible diaphragm is formed by a central portion of a cap engaged on said piston means, said cap also constituting a seal member between said piston means and the wall of said chamber.

10. A hypodermic syringe comprising:
    a body having a cylindrical wall terminating at one end with a needle mounting, said body providing a chamber to receive a liquid to be injected;
    a needle movably mounted in said mounting and having a terminal end located in said chamber, said terminal end having a head means;
    a piston slidably and sealingly located within said chamber and longitudinally movable so as to vary the volume of said chamber;
    operator manipulable means extending from said piston to enable a user to reciprocate said piston;
    wherein said piston includes gripping means to engage said terminal end of said needle when said chamber provides a minimum volume, so that subsequent movement of said piston to increase the volume of said chamber draws said needle into said chamber; and
    housing means in said manipulable means to receive said needle drawn into said chamber.

11. The syringe of claim 10 wherein said head means includes a head with an abutment surface, said gripping means includes a co-acting abutment surface to engage said abutment surface of said head.

12. The syringe of claim 10 wherein said piston includes a seal member which slidably and sealingly engages said cylinder wall, said seal member including a frangible diaphragm extending across said gripping means and which is ruptured by said head means when said gripping means is moved into engaging contact with said head means.

13. A syringe, comprising:
    a tubular body defining a chamber, said tubular body being open at one end to receive a plunger;
    a needle mounting at the other end of said tubular body;
    a needle means removably supported by said needle mounting and projecting from said needle mounting away from said tubular body, said needle means being carried by a needle support removably attached to said needle mounting, said needle support including shoulder means to engage corresponding shoulder means on said needle means preventing movement of said needle means axially with respect to said needle support and away from said tubular body, said needle means having an inner end within said chamber, said inner end being provided with a head means;
    piston means connected to said plunger and axially movable within said chamber, said piston means including engaging means for engaging shoulder means of said needle means located behind said head means when said piston means is moved within said chamber to said other end of said body whereby subsequent movement of said piston means towards said one end draws said needle means to draw said needle means into said chamber; and a frangible diaphragm means on said piston means, said head means further including a piercing end to rupture said diaphragm means on engagement of said engaging means with said head means.

14. The syringe according to claim 13 wherein said needle means engages within an axial bore in said needle support, the bore diameter and length being such as to frictionally hold said needle means in assembled position for use.

15. The syringe according to claim 13 wherein said needle means is provided with an enlargement which engages a corresponding groove in said needle support to hold said needle means in assembled position for use.

16. A hypodermic syringe, comprising:
a body having a cylindrical wall terminating at one end and providing a chamber to receive a liquid to be injected;
a needle assembly mounted in said one end of said chamber and incorporating a needle;
a needle housing within which said needle is secured, said needle housing being provided with head means;
a support to which said needle housing is removably attached, with said needle support being attached to a needle support mounting, said needle being movable in said needle support mounting;
a piston slidably and sealingly located within said chamber and longitudinally movable by operator manipulable means extending from sa id piston to enable a user to reciprocate said piston so as to vary the volume of said chamber;
said piston including gripping means to engage said needle when said chamber provides a minimum volume, so that subsequent movement of said piston to increase the volume of said chamber draws said needle into said chamber; and
housing means in said manipulable means to receive the needle drawn into said chamber.

17. The syringe of claim 16 wherein said needle housing is secured to said support by friction, which friction is overcome when said gripping means draws said needle into said chamber.

18. The syringe of claim 16 wherein said needle housing is mounted in said support by an interengaging annular rib and groove.

* * * * *

UNITED STATES PATENT AND TRADEMARK OFFICE
CERTIFICATE OF CORRECTION

PATENT NO. : 5,221,262
DATED : June 22, 1993
INVENTOR(S) : John P. Kite

It is certified that error appears in the above-indentified patent and that said Letters Patent is hereby corrected as shown below:

Column 2, line 42, delete "leas" and insert --least--

Column 4, line 17, delete "exist" and insert --exists--

Column 4, line 25, delete "24" and insert --26--

Column 4, line 64, after "atmosphere" insert --.--

Signed and Sealed this

Nineteenth Day of July, 1994

Attest:

BRUCE LEHMAN

*Attesting Officer*  *Commissioner of Patents and Trademarks*